US00PP16174P3

(12) United States Plant Patent
Layt

(10) Patent No.: US PP16,174 P3
(45) Date of Patent: Dec. 27, 2005

(54) ST. AUGUSTINE GRASS NAMED 'B12'

(50) Latin Name: *Stenotaphrum secundatum*
Varietal Denomination: B12

(75) Inventor: Todd Anthony Layt, New South Wales (AU)

(73) Assignee: Sod Solutions, Inc., Mt. Pleasant, SC (US)

( * ) Notice: Subject to any disclaimer, the term of this patent is extended or adjusted under 35 U.S.C. 154(b) by 99 days.

(21) Appl. No.: 10/663,928

(22) Filed: Sep. 16, 2003

(65) Prior Publication Data

US 2004/0205874 P1 Oct. 14, 2004

(30) Foreign Application Priority Data

Nov. 26, 2002 (AU) ..... 2002/342

(51) Int. Cl.[7] ..... A01H 5/00

(52) U.S. Cl. ..... Plt./392

(58) Field of Search ..... Plt./392

*Primary Examiner*—Anne Marie Grunberg
*Assistant Examiner*—Annette H Para
(74) *Attorney, Agent, or Firm*—Myers Bigel Sibley & Sajovec, P.A.

(57) ABSTRACT

'B12' is an attractive, green (RHS 137A) *Stenotaphrum secundatum* grass (St. Augustine grass), with a fast growth habit, brown with predominant yellow-green internode color, moderate internode length, and a long leaf blade that is highly infolded in mature turf, with a fine leaf appearance. 'B12' is also characterized by good disease and pest resistance and superior color retention under low fertilizer conditions.

7 Drawing Sheets

Latin name of the genus and species: The Latin name of the genus and species of the novel variety disclosed herein is *Stenotaphrum secundatum.*

Variety denomination: The inventive variety of St. Augustine grass disclosed herein has been given the variety denomination 'B12'.

BACKGROUND OF THE INVENTION

*Stenotaphrum secundatum* belongs to the grass family, Gramineae, and has the common names St. Augustine grass and buffalo grass. *Stenotaphrum secundatum* is a vigorous-growing perennial grass that prefers warm weather climates, and is able to withstand temperatures as high as 105° F. Its market class is turf grass, and it is widely used as a lawn grass in the Southern United States where many other grasses cannot survive the extreme temperatures.

Some commonly known varieties of *S. secundatum* include 'Floratine' (unpatented), 'Bitter Blue' (unpatented), 'Floratam' (unpatented), 'Seville St. Augustine' (unpatented), 'Raleigh St. Augustine' (unpatented), 'Texas Common' (unpatented), 'SS-100' (U.S. Plant Pat. No. 9,395; sold under the name PALMETTO™), 'Shademaster' (unpatented), 'Sir Walter' (Australian PBR No. 96/226; unpatented in the United States), and 'ST-85' (Australian Patent No. 643567; unpatented in the United States).

Lineage:

The variety 'B12' was identified in Spring 2001 in Clarendon, New South Wales, Australia, during a seedling selection of cultivated 'Sir Walter'. 'Sir Walter' is characterized by long-average internode length and intense purple intended color. Selection criteria for 'B12' were greener internode color and shorter internode length. The parent plant 'Sir Walter' was grown in isolation, and 5000 seeds were collected from open pollination in Spring 2000. These seeds were sown, and in February and March 2001, twelve of the resulting plants were selected based on their green stems. In Spring 2001 a final single selection, designated 'B12', was made from these twelve seedlings based on shorter internode length.

Asexual Reproduction:

'B12' was first asexually propagated by stolons in September 2001 in Clarendon, New South Wales, Australia. 'B12' has since been asexually propagated by means of stolons. The distinctive characteristics of the variety have remained stable and true to type through successive cycles of asexual propagation.

SUMMARY OF THE INVENTION

'B12' is an attractive, green (RHS 137A) *Stenotaphrum secundatum* grass (St. Augustine grass), with a fast growth habit, brown with predominant yellow-green internode color, moderate internode length, and a long leaf blade that is highly infolded in mature turf, with a fine leaf appearance. 'B12' is also characterized by good disease and pest resistance and superior color retention under low fertilizer conditions.

DETAILED BOTANICAL DESCRIPTION OF THE VARIETY

Figure 1:
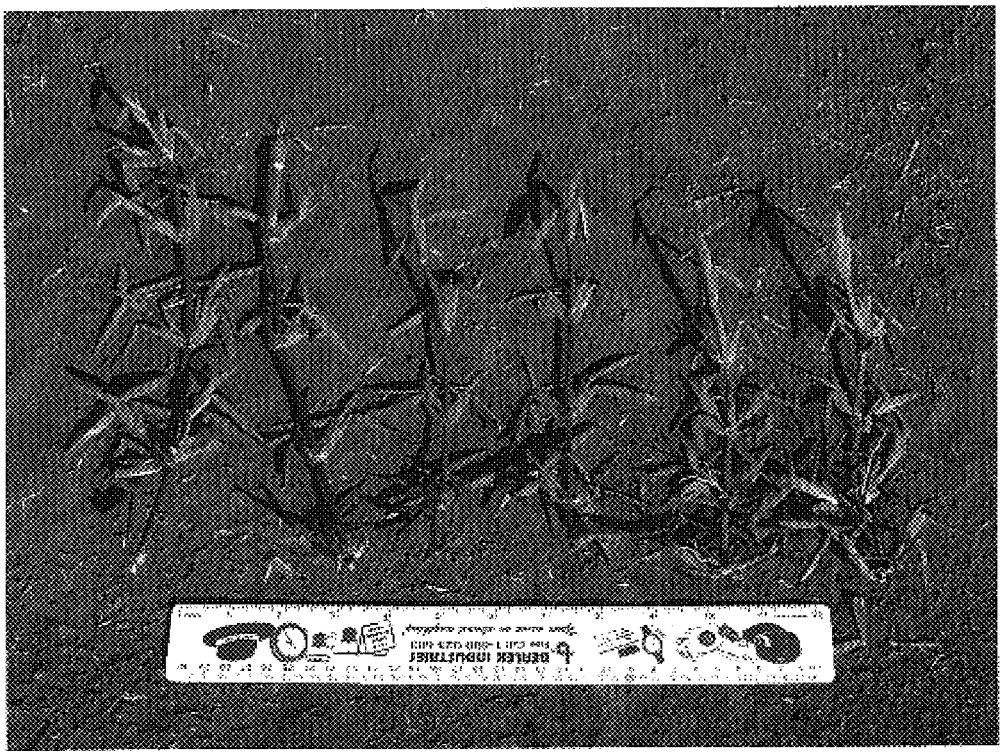
FIG. 1. Stolon length and color. Photo taken July 2003 in New South Wales, Australia showing the back view of the stolon. 'Sir Walter' with its longer internode length, and more purple internode is on the left. 'B12' with its medium internode length and its lighter colored internode is in the center. 'SS-100' is to the right with its shorter and greener internode.
Figure 2:
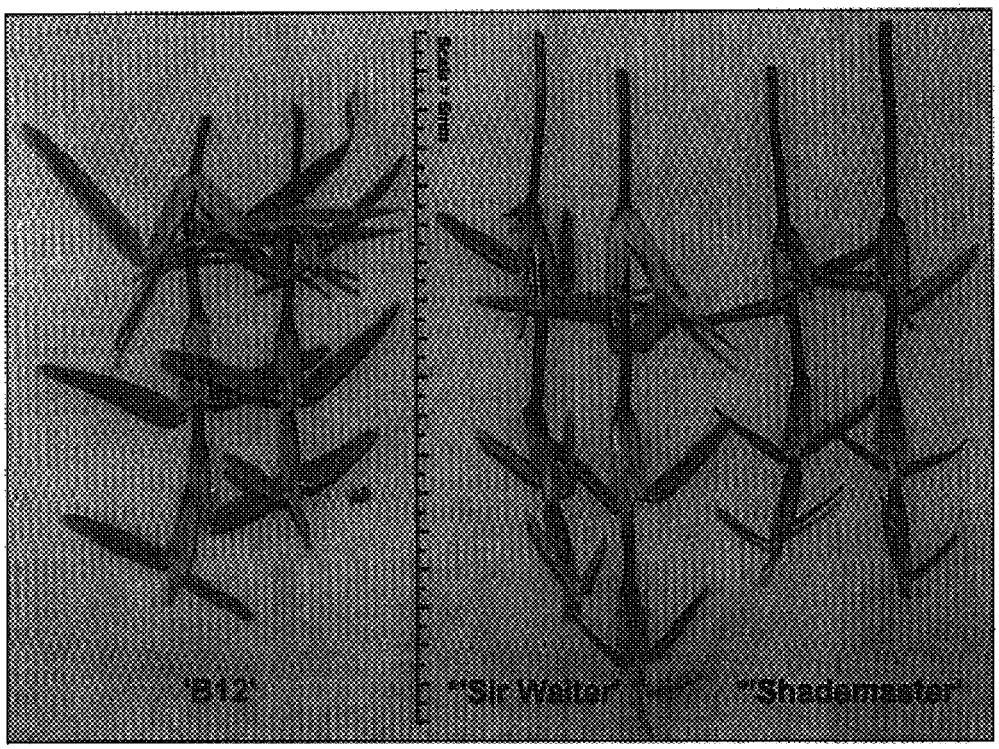
FIG. 2. *Stenotaphrum* 'B12' (left) with comparator 'Sir Walter' (center) and 'Shademaster' (right) showing differences in internode color.
Figure 3:
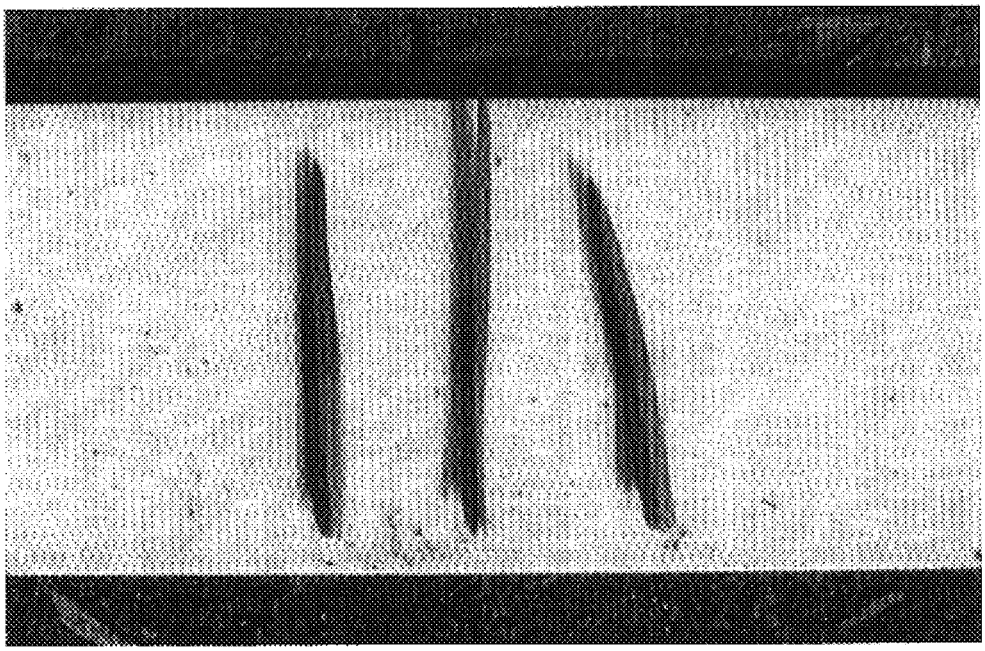
FIG. 3. Leaf angle comparison among 'SS-100' (left), 'B12' (middle), and 'Sir Walter' (right).
Figure 4:
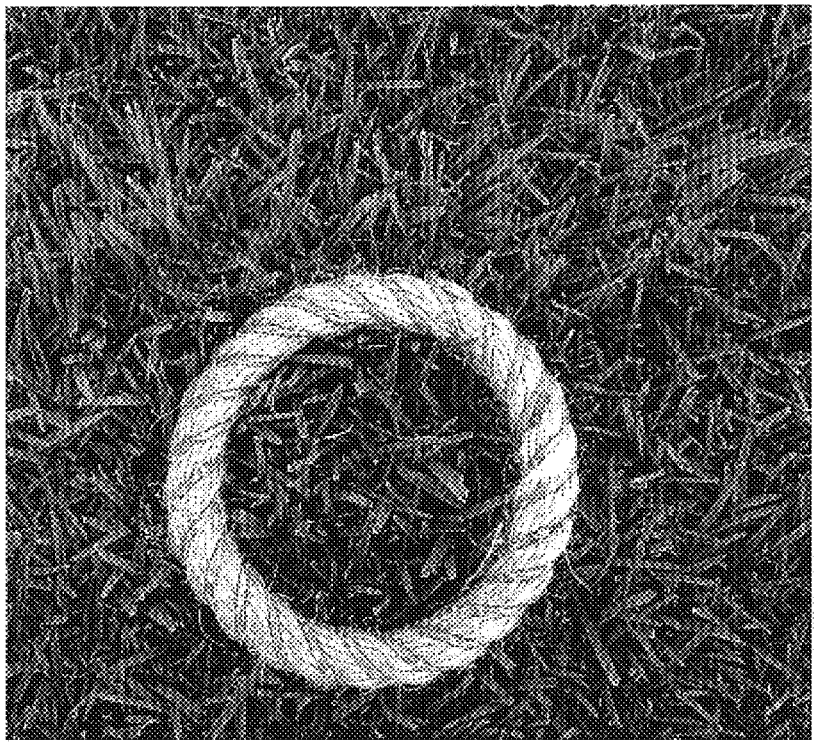
FIG. 4. 'B12' has a finer leaf and a higher frequency of acute leaf angles. Measurements for leaf angle trial (Comparison Trial 4) came from within this ring.
Figure 5:
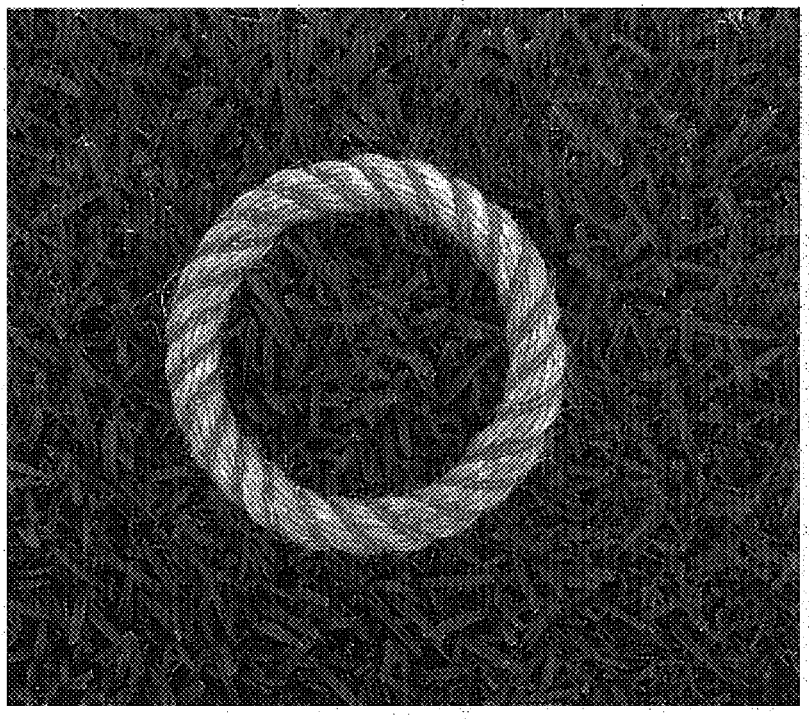
FIG. 5. 'Sir Walter' has a less fine leaf, and a higher frequency of less acute leaf angles. Measurements for leaf angle trial (Comparison Trial 4) came from within this ring.
Figure 6:
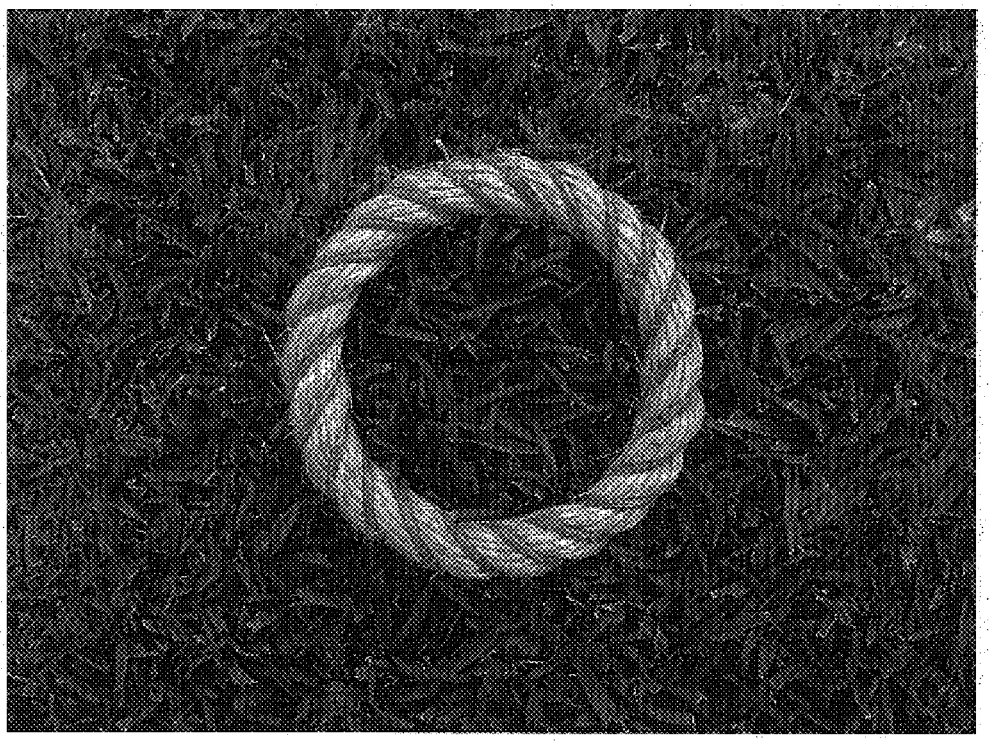
FIG. 6. 'SS100' has a less fine leaf, and a higher frequency of more open leaf angles than 'B12'. Measurements for leaf angle trial (Comparison Trial 4) came from within this ring.
Figure 7:
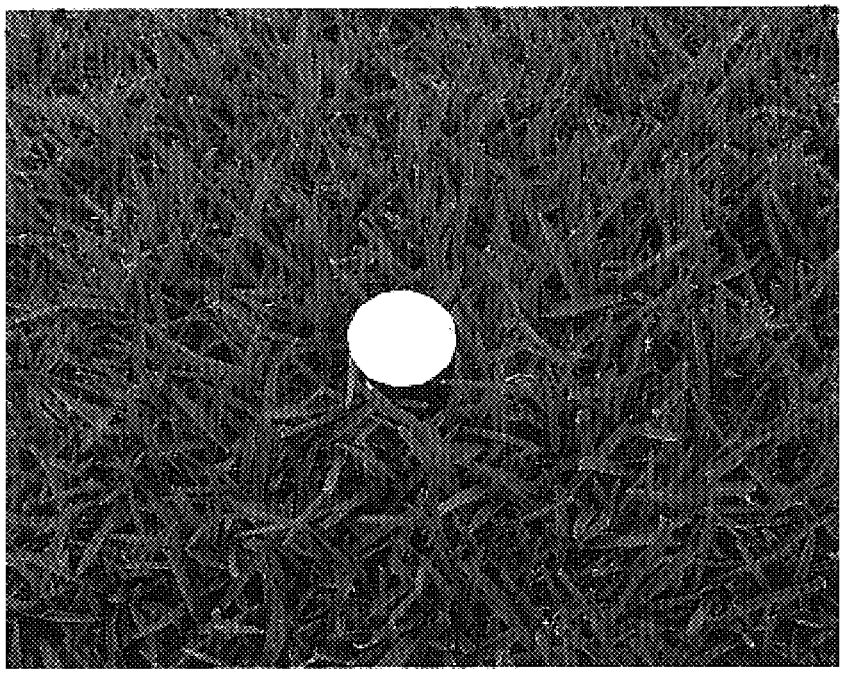
FIG. 7. 'B12' is shown as 18-month-old turf, illustrating its fine leaf appearance, with an Australian 50 cent piece in the picture.
Figure 8:
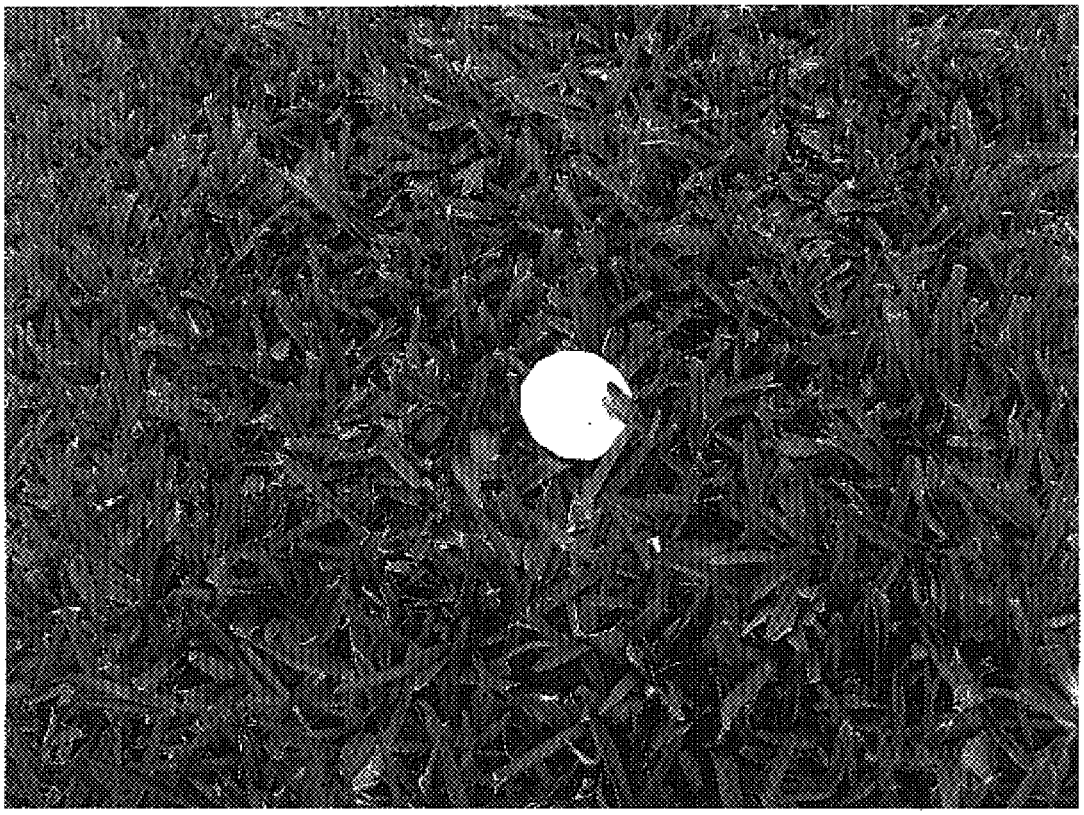
FIG. 8. 'Sir Walter' is shown as 18-month-old turf, illustrating its broader appearing leaf as compared with 'B12', with an Australian 50 cent piece in the picture.
Figure 9:
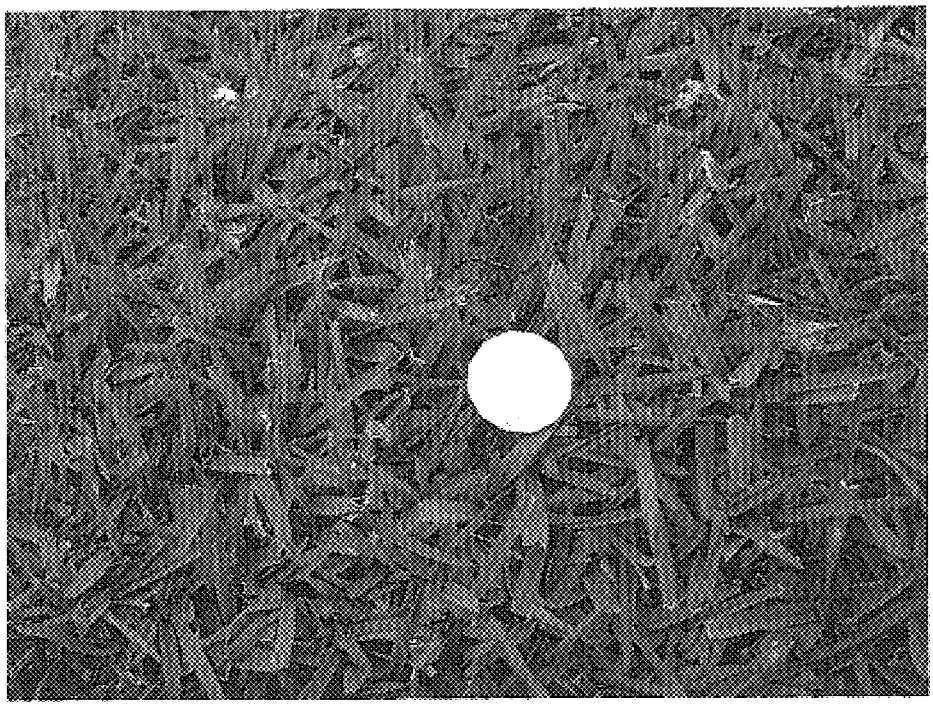
FIG. 9. 'SS100' is shown as 18-month-old turf, illustrating its broader appearing leaf as compared with 'B12', with an Australian 50 cent piece in the picture.
Figure 10:
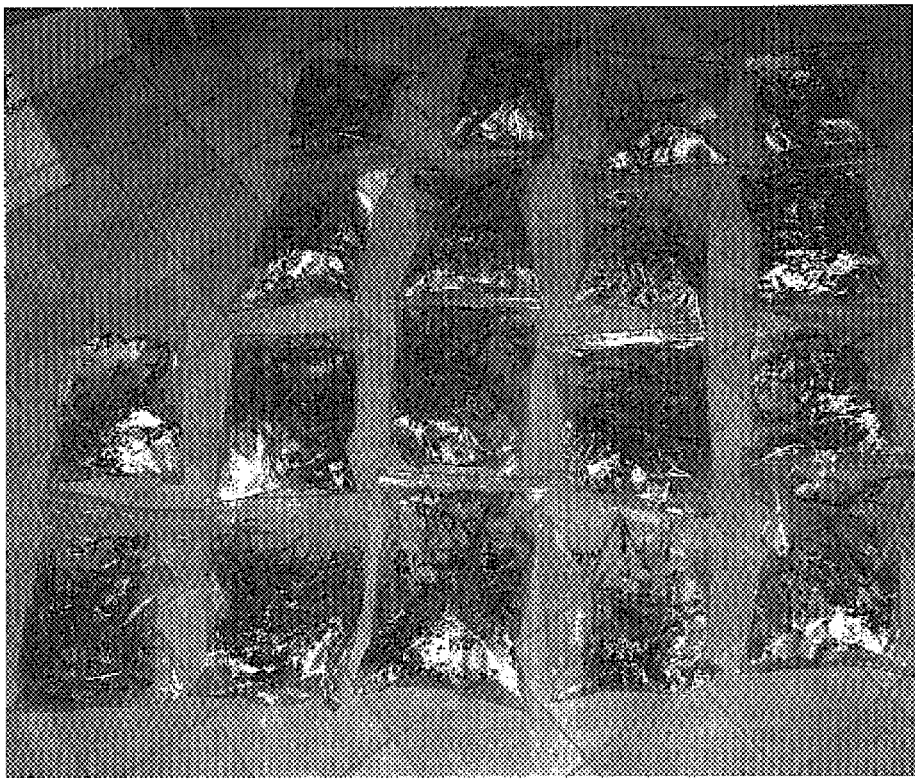
FIG. 10. Clippings collected from samples of each *Stenotaphrum* evaluated in the low fertilizer trials. At the end of the Kincumber trial, all vegetative material was harvested from each pot, placed in a plastic bag and weighed (see Table 8). 'B12' and 'SS-100' grew better with no fertilizer as compared with the other varieties.
Figure 11:
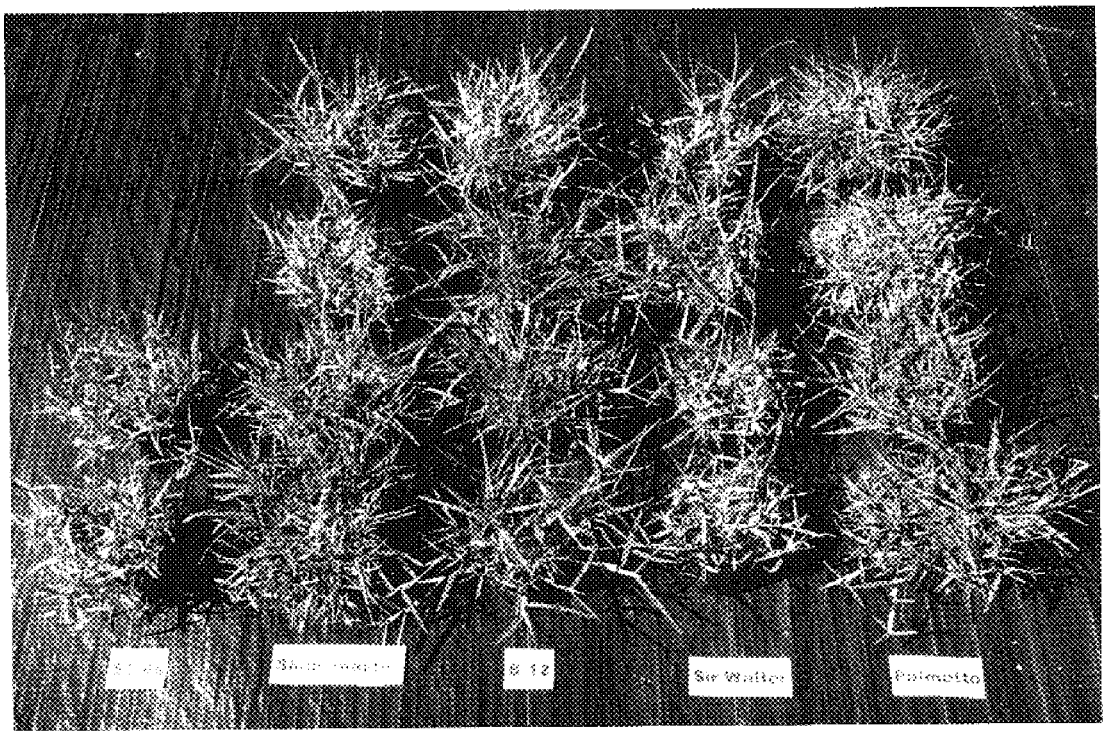
FIG. 11. Pots of the different *Stenotaphrum* showing the excellent growth of 'B12' and 'SS-100' (labeled as 'Palmetto') with no fertilizer. The long leaves of 'B12' can also be seen.

The following is a detailed botanical description of a new *Stenotaphrum secundatum* grass variety known as 'B12', based upon observations of the plant grown in nursery pots and field plots. Those skilled in the art will appreciate that certain characteristics will vary with older or, conversely, with younger plants. 'B12' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length, cultural conditions, and the like. Color notations are based on The Royal Horticultural Society Colour Chart, The Royal Horticultural Society, London (1995 edition).

'B12' is a perennial, vegetatively propagated *Stenotaphrum* grass, believed to be a variety of *Stenotaphrum secundatum*. The parent of 'B12' is 'Sir Walter' (Australian PBR no. 96/226; unpatented in the United States), a variety of *Stenotaphrum* widely grown in Australia. 'B12' is a fine leafed, fast-growing variety.

TECHNICAL DESCRIPTION OF THE VARIETY

The description of the variety below is taken from a pot trial conducted in the Spring/Summer 2002 in Clarendon, New South Wales, Australia. (Comparison Trial 1 below). Plants were six-months old at the time of observation. Additional characteristics of the plant are illustrated in FIGS. 1–11.

Plant characteristics: Perennial, stoloniferous grass, habit prostrate becoming erect when flowering, culms branched, glabrous.

Stolon: Roots at nodes, internode length (4th from tip) medium-long (mean 48.6 mm), average internode length (internodes 4 to 6 from tip) medium-long (mean 50.4 mm), color yellow-green (RHS 144A) at node changing to yellow-green (RHS 148A) along internode with diffuse brown (RHS 200A) becoming predominantly brown (RHS 200A) on upper exposed side of internode with maturity.

Leaf: Sheath length medium (mean 19.1 mm), color green (RHS 138B), leaf veins parallel and obscure, blade length medium (mean 20.2 mm), blade width medium (mean 6.4 mm), color green (RHS 137A), apex acute, leaf margin entire (smooth).

Ligule: Ligule is a hairy rim.

Awns: Absent.

Inflorescence: Spike-like panicle, length is 5.5 to 9 cm, color green (approximately RHS 137A).

Glumes and lemmas: Color green (RHS 137A) to yellow-green (RHS 146A); the upper glumes and lemmas are unequal in length as compared with the lower glumes and lemmas: the lower short, blunt, nerveless; the upper more acute and nerved.

Anther color: Greyed orange (between RHS 167A and 167B).

Stigma color: Purple violet (RHS 81A).

Seed: Seed is approximately 3 mm long and is rarely produced.

Cultural notes: 'B12' has been observed to survive to a temperature of −10° Celsius, and is heat and humidity tolerant. It has good drought tolerance, comparable with 'Sir Walter', and 'SS-100' (sold under the name PALMETTO™; U.S. Plant Pat. No. 9,395), with a strong and vigorous root system. 'B12' also grows well under low fertilizer conditions. Shade tolerance is good and is being further evaluated. 'B12' competes well with invasive weeds. It strikes well when being stolonised, and transplants well as sod.

Disease resistance: 'B12' appears to be resistant to grey-leaf spot as the observed occurrence of this disease has been very low (see also Table 13 below). The variety has reduced susceptibility to fungus and heat stress, and retains good summer color (i.e., does not show significant yellowing in summer).

Winter color: 'B12' has good winter color, being one of the last *Stenotaphrum secundatum* to go dormant, but under severe repeated frost it will turn brown.

COMPARISON TRIALS WITH OTHER VARIETIES IN AUSTRALIA

A series of comparative trials were carried out among 'B12', 'Sir Walter', 'SS-100', 'ST-85' (Australian Patent No. 643567; not patented in the United States) and 'Shademaster' (unpatented; a commonly-grown Australian variety).

The characteristics used to identify the most similar varieties of common knowledge to 'B12' were: plant characteristics, main color of the stolon, internode length, and leaf width and length. Based on these criteria, 'Sir Walter' and 'SS-100' were selected as the most similar comparators. For a broader comparison, although these varieties are readily distinguishable by stolon color alone, varieties 'ST-85' and 'Shademaster' were also included in some of the trials.

The results of the comparison trials are shown in Tables 1–8 below. In summary:

'B12' has a shorter internode length than 'Sir Walter', and a longer internode length than 'SS-100' and 'ST-85'.

'B12' has a longer leaf than 'ST-85', 'SS-100', 'Sir Walter' and 'Shademaster'.

'B12' has an internode color of brown with predominant yellow green, while 'SS100' has a green internode, 'Sir Walter' has an internode of dark purple with a little green, and 'ST-85' and 'Shademaster' have a dark purple internode color.

'B12' grows at a similar speed to 'Sir Walter', as determined by both stolon growth across the ground and upward leaf growth. Both grasses have similar mowing rates. 'B12' grows only modestly faster across the ground from stolons than does 'SS100', but grows significantly faster in the leaf, therefore requiring more mowing than 'SS-100'. It is noted that 'B12' grows unusually fast for a fine leaf *Stenotaphrum secundatum*. 'ST-85' is a more typical fine leaf variety, which grows more slowly than 'B12' in the leaf and stolon.

With respect to leaf width, it was determined that 'B12' has a finer leaf than 'Sir Walter', 'Shademaster', and 'SS100'. Further, when 'B12' is established and forms a dense mat, it has a more angled infolded leaf than 'Sir Walter' and 'SS100', which gives 'B12' the appearance of being even more fine leafed than these other varieties. The angled leaf of 'B12' enhances the fine leafed appearance and makes it visually appear to be much more than 1 mm finer than 'SS-100'.

Under conditions of low fertilizer, the best visual appearance ratings were for 'B12' and 'SS-100', followed by 'Shademaster'. The poorest visual appearance rating was for 'Sir Walter' followed by 'ST-85'.

In general, the varieties with highest visual ratings under low fertilizer conditions also had the highest scores for uniformity, density and greenness.

The comparison trials and results are described in more detail below.

Australian Comparison Trial 1: Internode Color, Internode Length and Leaf Length A comparative trial was conducted in Clarendon, New South Wales, Australia in Spring/Summer 2002. 'B12', 'Sir Walter', 'Shademaster', 'SS100' and 'ST-85' were compared for stolon color (i.e., internode color), leaf length and internode length. Individual stolons were taken from open beds, and were then planted in 140 mm pots filled with soiless potting mix. Nutrition was maintained with slow release fertilizers, which were added at the time the *Stenotaphrum* were potted. The plants were grown in full sun in the open, with irrigation. The pots were seven months old at the time of trial. The plants did not flower during the trial. The trial design consisted of thirty pots of each variety arranged in a completely randomized design. Measurements were taken in December 2002. The results are shown in Table 1 below.

TABLE 1

| | 'B12' | 'Sir Walter' | 'Shade-master' | 'SS100' | 'ST-85' |
|---|---|---|---|---|---|
| Internode Color (overall appearance) | Brown with predominant yellow-green | Dark purple with little green | Dark purple | Green | Dark Purple |
| Leaf Length (mm) - 4th node from tip | | | | | |
| mean | 20.2 | 17.2 | 15.2 | 14.5 | 10.7 |
| standard deviation | 4.2 | 1.5 | 1.7 | 2 | 1.7 |
| LSD/sig | 3.13 | Ns | P ≦ 0.01 | P ≦ 0.01 | P ≦ 0.01 |
| Average Internode Length (mm) - internodes 4 to 6 | | | | | |
| mean | 50.4 | 57.1 | 52.3 | 44.1 | 34.85 |
| standard deviation | 4.6 | 4.8 | 2.9 | 3.1 | 2.9 |
| LSD/sig | 4.76 | P ≦ 0.01 | ns | P ≦ 0.01 | P ≦ 0.01 |

Australian Comparison Trial 2: Leaf Width and Intended Length

Another comparison trial was conducted in Clarendon, New South Wales, Australia in October 2002, wherein three one-foot square pieces of sod of 'B12', 'Sir Walter' and 'SS-100' were compared with respect to internode length and leaf width. The sod was from Comparison Trial 3 below, and was planted in February 2002. The ten-month old sod was grown using standard practices in the sod industry, and was harvested with a spade. Seventy-eight random samples were taken, 26 from each piece of sod, and were examined for internode length and leaf width. The results are shown in Table 2. Note that results for pot-grown samples will differ from turf-grown samples. For example, when the turf starts to mat in the pot, its growth is constrained, which affects some measurements. In addition, mowing turf-grown samples will affect some measurements. The pot trials, however, are useful for showing trends, and the observed trends were consistent throughout the trials.

TABLE 2

| | 'B12' | 'SIR WALTER' | 'SS-100' |
|---|---|---|---|
| Leaf width (mm) - 4th node from tip | | | |
| Mean | 5.7 | 6.633 | 6.3 |
| Std deviation | 1.2 | 1.1 | 1.1 |
| LSD/sig | 0.7 | P ≦ 0.01 | P ≦ 0.01 |
| Average internode length | | | |
| Mean | 30.04 | 39.87 | 25.23 |
| Std deviation | 15 | 16.3 | 12.4 |
| LSD/sig | 9.1 | P ≦ 0.01 | ns |

Australian Comparison Trial 3: Time to Harvest

In a third study, carried out in February 2002, approximately 15 square meters of bare ground in a plot in Clarendon, New South Wales, Australia was planted with stolons of 'B12', 'Sir Walter', 'SS100' and 'ST-85'. These plots were mown, watered and fertilized regularly, and were monitored for 12 months. At 9 months, 'B12' and 'Sir Walter' were ready to harvest. At 9 months and 2 weeks, 'SS100' was ready to harvest. Both 'Sir Walter' and 'SS-100' are considered fast-growing varieties of *Stenotaphrum secundatum*. In the same trial, 'ST-85' was not ready for harvest for another 2 months and 2 weeks (i.e., at 12 months). The results of this comparison are shown below in Table 3. Readiness for harvest was judged by ability to harvest the turf with a hand turf cutter.

TABLE 3

| Variety | Time from Planting to Harvest |
|---|---|
| 'B12' | 9 Months |
| 'Sir Walter' | 9 Months |
| 'SS-100' | 9 Months 2 weeks |
| 'ST-85' | 12 Months |

Australian Comparison Trial 4: Leaf Width and Angle Comparison

In July 2003, a fourth trial comparing leaf width and leaf angle was conducted with 'Sir Walter' and 'SS-100', the two varieties of *Stenotaphrum secundatum* that were determined to be the most similar to 'B12'. Upon inspection of mature, never-harvested material from Comparative Trials 2 and 3 above, it was observed that 'B12' had a finer leaf appearance than the leaf measurements in the first trials suggested. For this reason, a second comparison of leaf measurements was conducted. The results are shown in Table 4.

TABLE 4

| | 'B12' | 'SIR WALTER' | 'SS-100' |
|---|---|---|---|
| Leaf width (mm) - 4th node from tip | | | |
| Mean | 4.85 | 6.02 | 5.88 |
| Std deviation | 0.8 | 0.9 | 0.7 |
| LSD/sig | 0.48 | $P \leqq 0.01$ | $P \leqq 0.01$ |

As expected, the comparison demonstrated that the leaf of 'B12' was finer than the leaves of the other two varieties. Nonetheless, it was surprising that the measurements indicated that 'B12' was only about 1 mm finer in leaf blade width. Based on visual appraisal of the varieties, 'B12' would appear to be at least 2 mm to 2.5 mm finer. Upon closer inspection and evaluation, it was noted that the leaf of 'B12' was far more infolded than the leaf of 'Sir Walter' and 'SS100'. A system of measuring was devised by bending small pieces of wire at 40 degrees, 80 degrees, 120 degrees, and 150 degrees. A series of measurements was taken from each grass. All samples had leaf angles that fell below 180 degrees. Any sample that could not be clearly measured (e.g., borderline cases) was discarded. In total, six samples were discarded: three from 'SS-100', two from 'Sir Walter' and one from 'B12'.

The results of this study can be seen in Table 5 below. It was found that 'B12' was more tightly infolded than the other varieties, as more of its leaves were folded at shaper angles, and less were folded at open angles. The somewhat finer leaf of 'B12', in combination with the more acute infold angle of the leaf, results in 'B12' having a much finer appearance than 'Sir Walter' and 'SS-100'.

TABLE 5

| Angle | 0 to 40° Extremely angled | 41 to 80° Highly angled | 81 to 120° Angled | 121 to 150° Open | 151 to 180° Very open |
|---|---|---|---|---|---|
| Category | 5 | 4 | 3 | 2 | 1 |
| Frequency of angle for 'B12' | 6 | 16 | 13 | 4 | 1 |
| Frequency of angle for 'Sir Walter' | 1 | 8 | 12 | 12 | 7 |
| Frequency of angle for 'SS-100' | 3 | 10 | 16 | 8 | 3 |

Australian Comparison Trials under Low Fertilizer Conditions

*Stenotaphrum* varieties held at Kincumber, New South Wales, Australia since December 2002 were rated for performance on Mar. 21, 2003. The turf was in 140 mm pots and was transferred to Kincumber from the plants used in Comparison Trial 1, described above. The turf had not received fertilizer and was minimally watered. The plants were cut back (to pot edge) approximately four weeks prior to evaluation. Each variety was assessed for the indices shown in Table 6.

TABLE 6

| Variety | Reps | Visual rating | Uni-formity | No. flower-ing | Leaf length | Density | Green-ness |
|---|---|---|---|---|---|---|---|
| 'B12' | 4 | 8–9 | 8–9 | 25% | long | 8–9 | light green (RHS 144A) |
| 'Shade-master' | 4 | 7–8 | 8–9 | 0% | med-long | 8 | light green (RHS 144A) |
| 'SS-100' | 4 | 8–9 | 9 | 0% | med-long | 9 | medium green (RHS 146A) |
| 'Sir Walter' | 4 | 5–6 | 5 | 25% | med-long | 5–6 | yellow-green (RHS 144A–B) |
| 'ST 85' | 2 | 5–6 | 8 | 100% | short | 8 | light green (RHS 144B) |

Performance Ratings:
Visual rating: 0 = dead, 10 = vigorous habit
Uniformity: 0 = poor, 10 = perfectly even over all replicates
Density: 0 = very sparse, 10 = very dense
Greenness: yellow-green (chlorotic, nutrient deficient), light green, medium green, dark green (no nutrition deficiencies apparent).

The remaining trial stock at Clarendon, New South Wales, Australia from Comparison Trial 1 was evaluated in the same way on Mar. 26, 2003. These plants were adequately watered, but were not fertilized or pruned. Results are shown in Table 7.

TABLE 7

| Variety | Reps | Visual rating | Uni-formity | No. flower-ing | Leaf length | Density | Green-ness |
|---|---|---|---|---|---|---|---|
| 'B12' | 20 | 9 | 9 | 100% | long | 8–9 | light green (RHS 144A) |
| 'Shade-master' | 20 | 8 | 8 | 25% | med | 8 | light green (RHS 144A) |
| 'SS-100' | 20 | 9 | 9 | 100% | med-long | 8 | medium green (RHS 146A) |
| 'Sir Walter' | 20 | 5–6 | 5–6 | 50% | med-long | 5–6 | yellow-green (RHS 144A–B) |
| 'ST-85' | 20 | 6–7 | 9 | 100% | short | 8–9 | Light green (RHS 144B) |

Performance Ratings:
Visual rating: 0 = dead, 10 = vigorous habit
Uniformity: 0 = poor, 10 = perfectly even over all replicates
Density: 0 = very sparse, 10 = very dense
Greenness: yellow green (chlorotic, nutrient deficient), light green, medium green, dark green (no nutrition deficiencies apparent).

The Kincumber stock (from the study shown in Table 6) was then harvested to determine average shoot yield as assessed by measuring the fresh weight of all above ground parts (leaves and stolons). Results are shown in Table 8.

TABLE 8

| Variety | Mean Shoot Fresh Weight (g) |
|---|---|
| 'B12' | 80 |
| 'Shademaster' | 71 |
| 'SS-100' | 105 |
| 'Sir Walter' | 39 |
| 'ST 85' | 55 |

Conclusions of Low Fertilizer Trials

The best visual appearance ratings were for 'B12' and 'SS-100', followed by 'Shademaster'. The poorest visual appearance rating was for 'Sir Walter' followed by 'ST-85'.

In general, the varieties with highest visual ratings also had the highest scores for uniformity, density and greenness. In other words, these varieties have complete ground coverage, even growth and a greener appearance than the poorer varieties.

Since the plants in these studies were not mown, it appears that longer leaf length combined with uniform growth generally contribute to a positive visual assessment. Leaf length correlated with shoot mass for the longer leaf varieties 'B12' and 'SS-100'.

Comparison Trials with other Varieties in the Southern United States

In April 2004, comparative evaluations began for the purpose of further quantifying characteristics of 'B12'. Twenty-two evaluation sites across the southern United States were selected to host these evaluations (sites were located in Virginia, North Carolina, South Carolina, Georgia, Florida, Alabama, Louisiana, Arkansas, Texas, New Mexico and Arizona). Each site was constructed to a specified protocol that comprised: pre-plant herbicide application, plot dimensioning and configuration, replication instruction, establishment regimen, and maintenance guidelines.

At each site, 'B12' was compared to other local "standard" St. Augustine grass varieties (each site used two or three standard varieties for comparison, specifically 'SS-100' (sold under the name 'PALMETTO'™), 'Raleigh St. Augustine' and/or 'Floratam'). All sites were constructed with three replications of each variety used. Plots measured 8'×8' and observations were made on 30 day intervals, beginning 30 days after planting (DAP). Evaluation criteria included Overall Turf Quality, Color, Presence of Seed Head/Flowers, Ground Coverage, Internode Length, Disease Presence, and Insect Damage.

90 DAP Results.

In August 2004, observations from eight representative sites (see Table 9) were collected and analyzed. When compared to observations made on the standard St. Augustine grass varieties, several distinguishing characteristics of 'B12' became apparent. These findings are discussed below:

Overall Turf Quality

Compared to St. Augustine grass varieties 'SS-100', 'Raleigh St. Augustine' and 'Floratam', 'B12' was characterized as developing a higher overall turf quality at the 30, 60 and 90 DAP observations (see Table 10).

Color

'B12' consistently exhibited a more pleasing genetic color than 'SS-100', 'Raleigh St. Augustine' or 'Floratam'. This characteristic was most notable during 60 and 90 DAP observations (see Table 11).

Ground Coverage

The rate at which 'B12' grew to cover its test plots was significantly faster than that of 'SS-100' or 'Raleigh St. Augustine'. Although the difference was not as significant when compared to 'Floratam', an increased coverage rate was also observed (see Table 12).

Disease

The occurrence of disease, specifically gray-leaf spot, was notably lower in 'B12' and 'Raleigh St. Augustine' at 90 DAP. At 60 DAP; 'B12', 'SS-100' and 'Raleigh St. Augustine' all had a much lower occurrence of gray-leaf spot than 'Floratam' (see Table 13).

Internode Length

'B12' has a longer internode length than 'SS-100', 'Raleigh St. Augustine' or 'Floratam' when measured between nodes 3 and 4 from the tip of the stolon (see Table 14).

TABLE 9

Comparative Evaluation Sites

| Site # | Site Location | Varieties Evaluated 'B12' | 'SS-100' | 'Raleigh' | 'Floratam' |
|---|---|---|---|---|---|
| 1 | Kenansville, FL | Yes | Yes | No | Yes |
| 2 | Arcadia, FL | Yes | Yes | No | Yes |
| 3 | Awendaw, SC | Yes | Yes | Yes | No |

TABLE 9-continued

| Site # | Site Location | Varieties Evaluated 'B12' | 'SS-100' | 'Raleigh' | 'Floratam' |
|---|---|---|---|---|---|
| 4 | Raeford, NC | Yes | Yes | Yes | No |
| 5 | Boling, TX | Yes | Yes | Yes | No |
| 6 | Pilot Point, TX | Yes | Yes | Yes | No |
| 7 | San Antonio, TX | Yes | Yes | Yes | No |
| 8 | Crosby, TX | Yes | Yes | Yes | No |

TABLE 10

Overall Turf Quality (Average on 1–9 Scale; 9 = Ideal Turf)

| St. Augustine Grass Variety | Days After Planting (DAP) 30 | 60 | 90 |
|---|---|---|---|
| 'B12' | 7.4 | 7.8 | 7.9 |
| 'SS-100' | 6.8 | 6.8 | 6.2 |
| 'Raleigh' | 7.1 | 7.1 | 6.8 |
| 'Floratam' | 6.5 | 5.3 | 5.2 |

TABLE 11

Color (Average on 1–9 Scale; 9 = Ideal Color)

| St. Augustine Grass Variety | Days After Planting (DAP) 30 | 60 | 90 |
|---|---|---|---|
| 'B12' | 7.3 | 7.5 | 7.6 |
| 'SS-100' | 6.8 | 6.8 | 6.4 |
| 'Raleigh' | 7.2 | 7.1 | 6.9 |
| 'Floratam' | 6.7 | 5.2 | 6.3 |

TABLE 12

Ground Coverage (Average Percent Cover)

| St. Augustine Grass Variety | Days After Planting (DAP) 30 | 60 | 90 |
|---|---|---|---|
| 'B12' | 31% | 75% | 93% |
| 'SS-100' | 21% | 45% | 66% |
| 'Raleigh' | 24% | 47% | 69% |
| 'Floratam' | 27% | 68% | 90% |

TABLE 13

Disease (Average Disease Presence on 1–9 Scale; 9 = No Disease)

| St. Augustine Grass Variety | Days After Planting (DAP) 30 | 60 | 90 |
|---|---|---|---|
| 'B12' | 9.0 | 7.6 | 7.7 |
| 'SS-100' | 9.0 | 7.9 | 6.8 |
| 'Raleigh' | 9.0 | 7.9 | 7.7 |
| 'Floratam' | 9.0 | 5.3 | 5.2 |

TABLE 14

Internode Length (Average from 3rd to 4th in millimeters)

| St. Augustine Grass Variety | Days After Planting (DAP) 60 | 90 |
|---|---|---|
| 'B12' | 50.8 | 58.4 |
| 'SS-100' | 38.1 | 48.3 |
| 'Raleigh' | 48.3 | 45.7 |
| 'Floratam' | 43.2 | 48.3 |

Summary

Comparative observations of 'B12' were taken as part of an on-going multi-site, geographically diverse, evaluation regimen which began in April 2004. Analysis of these 30, 60, and 90 DAP observations clearly identified characteristics of 'B12' that differentiate it from 'SS-100', 'Raleigh' and 'Floratam' St. Augustine grasses. Notably, enhanced Turf Quality and Color augments the marketability of 'B12' as producers and consumers generally prefer turfgrass varieties that are more aesthetically pleasing. Increased Ground Coverage rates reduce production and overhead costs and provide turfgrass producers with larger profit margins and quicker harvest cycles. Also, reduced occurrence of Disease, specifically gray-leaf spot, lessens the need for fungicide inputs during production and end-use; reducing costs and minimizing potential environmental impacts from chemical applications. Finally, a distinguishing physical characteristic of 'B12' is its longer internode Length (as measured between the 3rd and 4th internode).

Comparative DNA Analysis of 'B12' with other Turfgrasses

Randomly Amplified Polymorphic DNA (RAPD) analysis of 'B12' in comparison with other turfgrasses was performed using a series of ten-mer primers from Operon Technologies, Inc. (Alameda, Calif.) as described below:

Plant material

Samples from six different turfgrasses were provided by Todd Bunnell, (Clemson University). The turfgrass varieties used in the analysis were: 'Bitterblue', 'PALMETTO'™, 'Woerner Classic', 'Raleigh St. Augustine', 'Floratam', and 'B12'.

DNA isolation

DNA was isolated from the leaf blades using the DNeasy procedure from Qiagen (Valencia, Calif.). The DNA extracts were quantified so that equal amounts of DNA could be used in the amplifications.

Amplification primers

One hundred ten-mer primers from Operon Technologies, Inc. (Alameda, Calif.) were used in the comparisons among the six turf grass samples. Of these, 32 were used to evaluate the complete set of samples (OPB 1, OPB 6, OPB 7, OPB 11, OPB 12, OPB 15, OPB 17, OPB 18, OPB 19, OPC 4, OPC 6, OPC 8, OPC 9, OPC 10, OPC 11, OPC 12, OPJ 7, OPJ 9, OPJ 10, OPJ 11, OPJ 13, OPK 1, OPK 4, OPK 10, OPK 11, OPK 15, OPAC 2, OPAC 3, OPAC 10, OPAC 11, OPAC 18, OPAC 19, OPAC 20)

Figure 12:
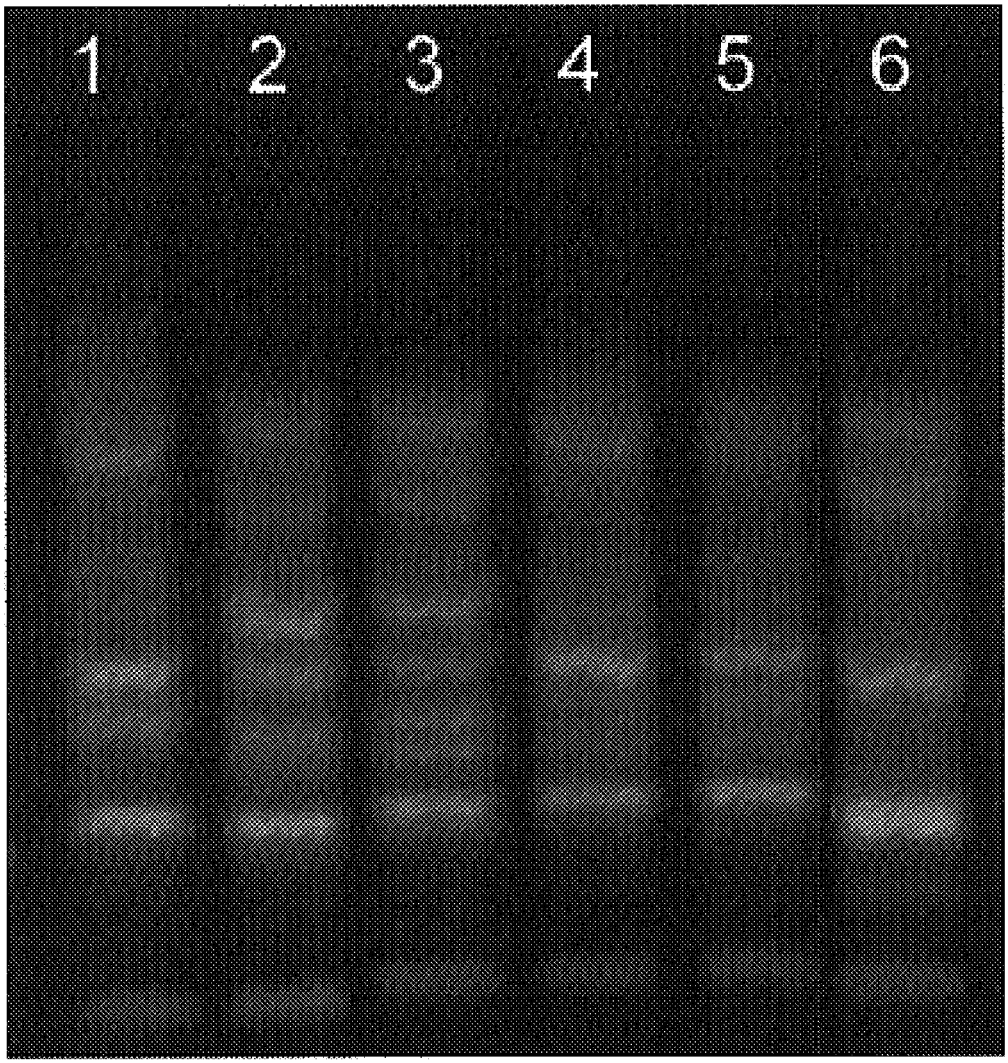
FIG. 12. PCR products separated on a 1.5% agarose gel in Tris-borate-EDTA containing ethidium bromide. PCR amplification products were visualized using a Bio-Rad transilluminator. Lane 1='Bitterblue'; Lane 2='SS-100' 'PALMETTO'™; Lane 3='Woerner Classic'; Lane 4='Raleigh St. Augustine'; Lane 5='Floratam'; Lane 6='B12'.

FIG. 12 shows the results when the primer OPC4 (CCGCATCTAC; SEQ ID NO:1) was used.

Amplification

The PCR reaction was carried out using TaKaRa Taq polymerase (Takara Bio Inc.) in the manufacturer's supplied buffer with a final concentration of $MgCl_2$ of 2.5 mM. Each reaction contained 25 $\mu$g of leaf DNA. The PCR reactions were subjected to a hot start with the buffer heated to 85° C. before the addition of Taq polymerase. All the reactions were carried out using MJR PTC-100 thermal cyclers (MJ Research, Inc.).

The amplification program consisted of:

1. 1 min 96° C.
2. 1 min 94° C.
3. 1 min 35° C.
4. 1 min 72° C.
5. Cycle to step 2 45 times.
6. Hold at 72° C. for 10 minutes.
7. Cool to 4° C.
8. Hold.

Gel electrophoresis and photography

The PCR products were separated on a 1.5% agarose gel in Tris-borate-EDTA containing ethidium bromide and visualized using a Bio-Rad transilluminator. Images were captured with a Kodak DC290 camera. Lane 1='Bitterblue'; Lane 2='PALMETTO'™; Lane 3='Woerner Classic'; Lane 4='Raleigh St. Augustine'; Lane 5='Floratam'; Lane 6='B12'.

RAPD analysis

Randomly Amplified Polymorphic DNA (RAPD) analysis of the six turfgrass samples was carried out as described above. All of the samples could be distinguished from each other using one or more of the ten-mer primers. The results with the OPC4 primer are shown in FIG. 12. As shown in the figure, 'B12' can be distinguished by RAPD analysis from the other turfgrasses evaluated using the OPC4 primer.

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial
<220> FEATURE:
<223> OTHER INFORMATION: Primer

<400> SEQUENCE: 1

ccgcatctac                                                    10
```

That which is claimed is:

1. A new and distinct variety of *Stenotaphrum secundatum* plant named 'B12', substantially as illustrated and described herein.

* * * * *

UNITED STATES PATENT AND TRADEMARK OFFICE

CERTIFICATE OF CORRECTION

PATENT NO. : PP 16,174 P3
DATED : December 27, 2005
INVENTOR(S) : Layt

It is certified that error appears in the above-identified patent and that said Letters Patent is hereby corrected as shown below:

Column 1,
Line 1, insert the following:

-- RELATED APPLICATION INFORMATION

This application claims the benefit of Australian Plant Breeders Rights Application Serial No. 2002/342, filed on November 15, 2002, received by the Australian Plant Breeders Rights Office on November 26, 2002, and accepted on December 13, 2002. --.

Signed and Sealed this

Sixth Day of June, 2006

JON W. DUDAS
*Director of the United States Patent and Trademark Office*